United States Patent
Mathis

[19]

[11] Patent Number: 6,129,692
[45] Date of Patent: Oct. 10, 2000

[54] NEUROPATHY RELIEF VACUUM TRACTION ASSIST SYSTEM FOR CARPAL TUNNEL RELIEF

[75] Inventor: Timothy Mathis, Rome, N.Y.

[73] Assignee: Inductive Technologies, Inc., Rome, N.Y.

[21] Appl. No.: 09/365,248

[22] Filed: Jul. 30, 1999

Related U.S. Application Data

[60] Provisional application No. 60/098,418, Aug. 31, 1998.

[51] Int. Cl.[7] .................................................. A61F 5/00
[52] U.S. Cl. .................................. 602/21; 602/5; 602/14; 602/20; 602/12
[58] Field of Search ...................................... 128/869, 870, 128/876, 877, 878, 879; 602/5, 14, 12, 20, 21, 60, 61, 62, 69, 6, 8; 2/455

[56] References Cited

U.S. PATENT DOCUMENTS

| | | | |
|---|---|---|---|
| 5,772,620 | 6/1998 | Szelma et al. | 602/21 |
| 5,810,753 | 9/1998 | Eberbach | 602/21 |
| 5,873,130 | 2/1999 | Lafferty | 2/16 |
| 5,916,187 | 6/1999 | Brill | 602/21 |
| 5,925,007 | 7/1999 | Ashline | 602/21 |
| 5,928,172 | 7/1999 | Gaylord | 602/21 |
| 5,987,641 | 11/1999 | Walker | 2/16 |
| 6,024,715 | 2/2000 | Maxwell | 602/64 |
| 6,063,087 | 5/2000 | Agee et al. | 606/55 |

*Primary Examiner*—Kim M. Lee
*Attorney, Agent, or Firm*—Sughrue, Mion, Zinn, Macpeak & Seas, PLLC

[57] ABSTRACT

An apparatus for relieving carpal tunnel syndrome is comprised of a support plate adapted to be mounted on the wrist of a wearer. An elevated bridge is mounted on the support plate out of contact with the wrist of the wearer. A soft, flexible patch is adhesively secured to the skin of the wrist opposite the support plate and an elastic device is adjustably connected between the patch and the bridge for applying a negative pressure to the carpal tunnel area.

5 Claims, 2 Drawing Sheets

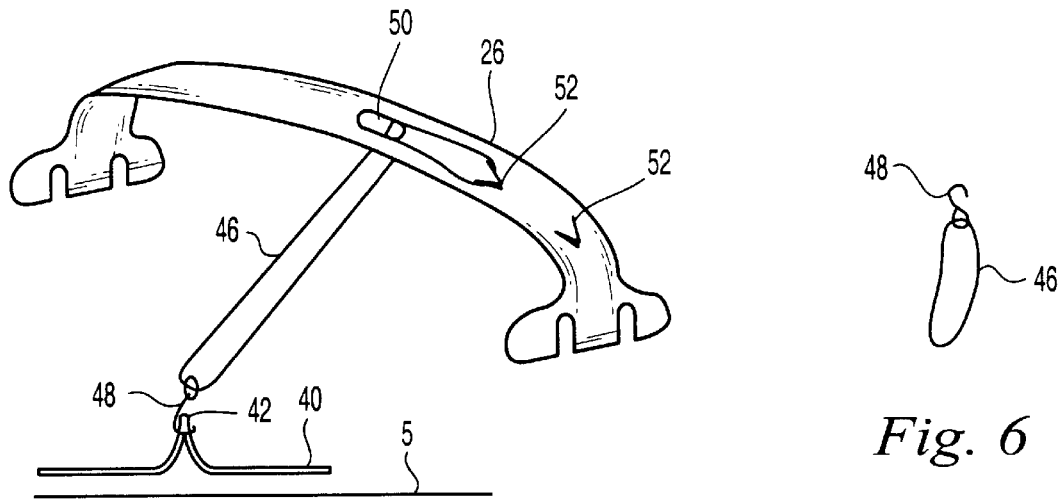
Fig. 5
Fig. 6
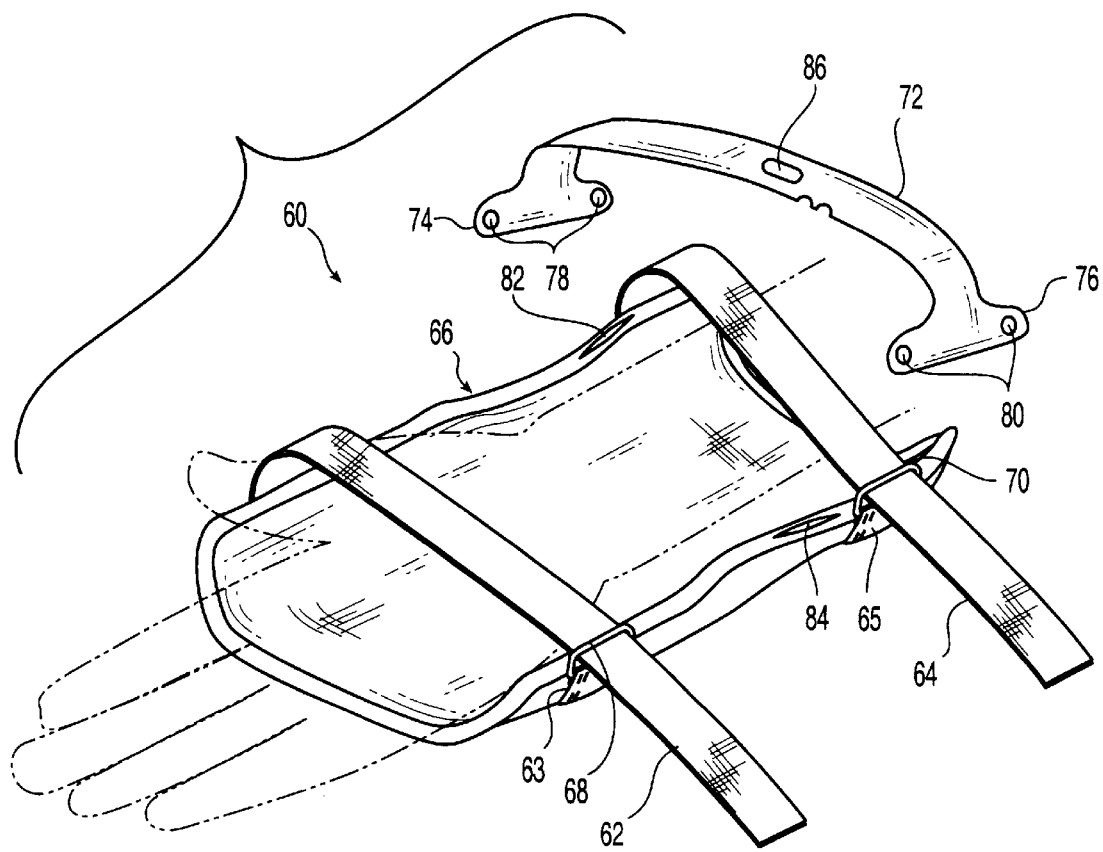
Fig. 7

NEUROPATHY RELIEF VACUUM TRACTION ASSIST SYSTEM FOR CARPAL TUNNEL RELIEF

This application claims benefit of U.S. Provisional Application No. 60/098,418 filed Aug. 31, 1998, the entire disclosure thereof being incorporated herein by reference.

BACKGROUND OF THE INVENTION

The present invention is directed to a neuropathy relief vacuum traction assist system and more specifically to an apparatus adapted to be mounted on the wrist for applying a negative pressure to the skin on the under side of the wrist to relieve the effects of carpal tunnel syndrome.

Carpal tunnel syndrome (CTS) is a very common and debilitating occupational illness affecting millions of people world wide. Carpal tunnel syndrome is the result of median nerve compression at the wrist. The carpal tunnel is a narrow channel that contains nine flexor tendons and the median nerve. The floor of the tunnel is formed by the concave-shaped carpal bones and the palmar wrist ligaments. The roof of the canal is formed by the transverse carpal ligament. The distal palmar wrist crease represents the level of the proximal border of the ligament. The thin antebrachial fascia blends with the thick transverse carpal ligament.

Median nerve compression in the carpal tunnel is caused by increased pressure in the carpal tunnel due to a discrepancy between the size of the canal and its contents. Normal pressure within the carpal tunnel is 2.5 mm Hg, increasing to approximately 30 mm Hg on full wrist flexion or extension. In patients with carpal tunnel syndrome, pressure is approximately 30 mm Hg within the tunnel and increases to 90 mm Hg on full wrist flexion or extension.

The pathogenesis of carpal tunnel syndrome can be related to anatomic, physiologic, pathologic and traumatic conditions. Anatomic structures include a thick ligament and a variety of congenital anomalies (persistent median artery, aberrant muscles). Conditions that alter fluid balance in the body may predispose one to carpal tunnel syndrome, as do tenosynovitis, osteoarthritis of the wrist and tumors. Occupational activities alone may not be causative but the condition is 15 times more prevalent in persons whose occupations place great physical demands on their hands, particularly repetitive wrist flexion and extension, intensive gripping and awkward wrist position. Malunion of a fracture of the distal radius can cause acute or delayed carpal tunnel syndrome. The most frequent symptoms of carpal tunnel syndrome are pain and paresthesias on the palmar aspect of the wrist and hand. The paresthesias are induced by activity, typically occur at night (a few hours after retiring), and are relieved by shaking or massaging the hand. Many patients complain that the hand feels "fat" or "swollen" and report that they feel weak and clumsy and that they drop objects. Strenuous or repetitive use of the hand such as grasping can aggravate the pain which may radiate to the wrist, elbow, forearm and shoulder.

In the past, the treatment of carpal tunnel syndrome depended on the cause and severity of the condition. In mild compression, wrist splinting and changing habits may suffice. An example of a wrist splint for carpal tunnel syndrome treatment is found in U.S. Pat. No. 5,417,645 granted May 23, 1995 to Roger D. Lemmen. Other types of devices for relieving the compression associated with carpal tunnel syndrome are disclosed in the U.S. patents to Davini (U.S. Pat. No. 4,966,137), Spitzer (U.S. Pat. No. 5,031,640), Sucher (U.S. Pat. No. 5,256,136) and Lair et al. (U.S. Pat. No. 5,466,215).

SUMMARY OF THE INVENTION

The present invention provides a new and improved system for relieving the symptoms associated with carpal tunnel syndrome. An adhesive patch is secured to the skin over the base of the wrist and is elastically supported from an overhead structure mounted on the wrist so that traction can be applied to the skin. As a result of this system, a sustained decrease in carpal tunnel pressure can be maintained. A reduction of just a few millimeters of mercury of pressure definitely relieves symptoms of CTS to break the vicious circle of deterioration by relieving the microischemia involved which ultimately alleviates the inflammation leading to a remission of CTS.

BRIEF DESCRIPTION OF THE DRAWINGS

FIG. 5 is a partial perspective view showing the relationship of the patch, the elastic member and the bridge.

FIG. 6 is a perspective view of the elastic member and hook.

FIG. 7 is an exploded view of a modified apparatus with the hand and wrist shown in phantom lines.

DETAILED DESCRIPTION OF THE INVENTION

Figure 1:
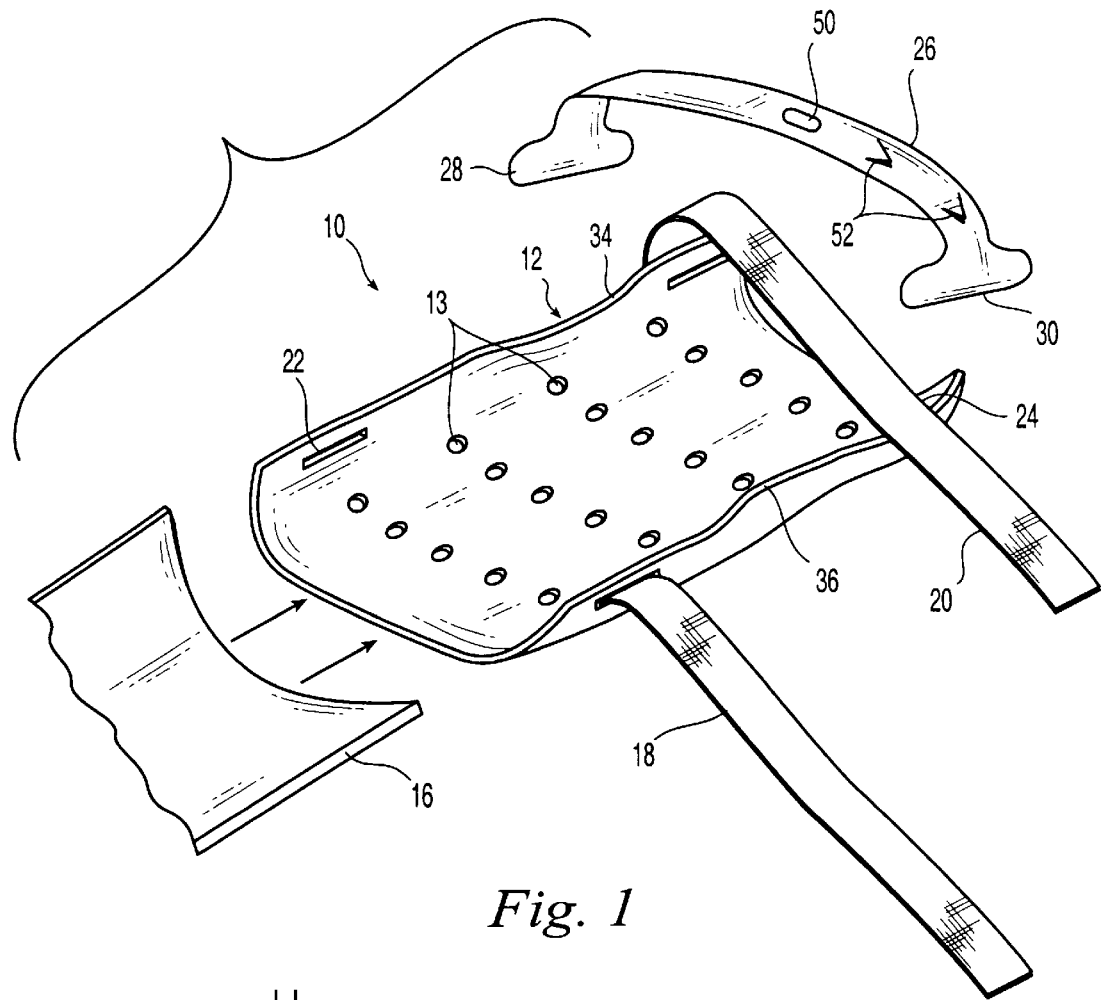
FIG. 1 is an exploded view of the apparatus according to the present invention adapted to be mounted on the wrist of a person.
Figure 2:
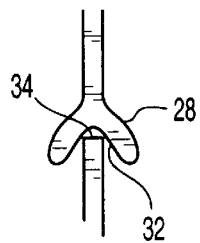
FIG. 2 is a partial sectional view showing the relationship of the bridge to the curved base plate when the bridge is mounted thereon.
Figure 3:
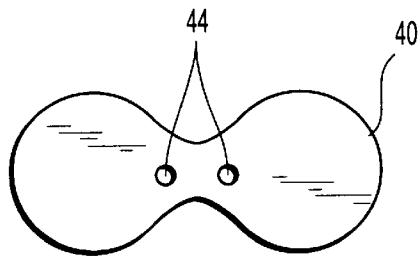
FIG. 3 is a plan view of the skin patch per se.

The apparatus 10, as shown in FIG. 1, is comprised of a semi-rigid support plate 12 adapted to be mounted on the back of the wrist and hand of a person. The longitudinal edges of the support plate 12 are curved upwardly and the support plate 12 may be additionally contoured to conform to the configuration of the wrist area. The support plate 12 is provided with a plurality of apertures 13 for ventilation purposes. The support plate 12 may be formed of any suitable semi-rigid material such as plastic, aluminum or the like. A soft pad 16 of any suitable material such a foamed plastic or the like has approximately the same dimensions as the support plate 12 and is adapted to be mounted between the support plate 12 and the wrist of a person wearing the apparatus. A pair of VELCRO® straps 18 and 20 are secured adjacent opposite ends of the support plate, respectively. The straps are adapted to extend over the wrist and hand of a wearer, through the slots 22 and 24, respectively and then are folded back for securement to the outer surfaces thereof. In this way, the support plate 12 is firmly secured to the wrist and hand of the wearer.

A bridge member 26 having curved end portions 28 and 30 is mounted on the support plate 12. The end portions 28 and 30 are each provided with an elongated groove 32 which fits over the upper edges 34 and 36, respectively, of the support plate 12.

Figure 4:
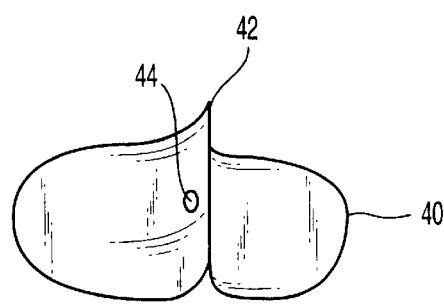
FIG. 4 is a perspective view of the skin patch in the folded condition for application to the skin.

A patch 40 of a soft material, such as MOLESKIN®, is provided for securement to the skin of the wrist opposite the support plate 12. The patch 40 may be secured to the wrist by any suitable adhesive, such as benzoin or the like. The patch has a FIG. 8 outline with two apertures 44 adjacent the reduced width portion of the patch. Thus, the patch may be folded in the manner shown in FIG. 4 with the reduced width portion pulled upwardly to form a crease 42. Thus, the apertures 44 in the patch, will be aligned with each other.

An elastic loop 46, which may be comprised of a rubber band or suitable equivalent, has a hook 48 secured thereon. The hook is adapted to engage the aligned apertures 44 in the patch when the patch is folded in the condition as shown in FIG. 5. The elastic loop 46 is extended through an aperture 50 in the center of the bridge 26 and secured under a selected one of a plurality of tabs 52, as shown in FIG. 5. When the patch 40 is adhesively secured to the skin S and the bridge 26 is mounted on the edges of the support plate 12, the elastic loop 26 will be tensioned to the desired degree, depending upon the tab 52 with which it is engaged. This tends to pull the skin outwardly of the wrist, thus effectively providing a negative pressure in the area of the carpal tunnel to relieve the pressure on the median nerve.

The fact that the patch 40 is adhesively secured to the skin and the elastic loop 46 is secured to the bridge 26 under tension will hold the bridge in position on the support plate 12. Additional securement means may be provided for holding the bridge in the desired position on the support plate 12.

A modified form of the apparatus 60 is shown in FIG. 7, wherein the support plate (not shown) which is similar to the support plate 12 in FIG. 1, is completely enclosed by a fabric cover 66. A pair of VELCRO® straps 62 and 64 are secured to the fabric cover 66 by stitching 63 and 65. A pair of loops 68 and 70 are secured to one end of the straps, respectively. The straps 62 and 64 extend over the hand and wrist of a person wearing the apparatus, pass through the loops 68 and 70 and are then folded back for securement to themselves.

A bridge member 72 is provided, similar to the bridge member 26. However, the opposite ends 74 and 76 of the bridge member 72 are provided with holes 78 and 80. Corresponding holes (not shown) are provided adjacent the edges of the support plate whereby the bridge member 72 can be secured to the support plate by means of rivets (not shown) extending through the mating apertures in the bridge member and the support plate. The bridge member 72 will extend outwardly of the fabric covering through the openings 82 and 84.

The bridge member 72 is provided with a central aperture 86 through which the elastic members 46 shown in FIG. 6, would extend. In this embodiment, the elastic member 46 would then be secured to a projection 88 along one edge of the bridge member 72 in lieu of the tabs 52 shown in the previous embodiment. Additional projections 88 can be provided along the edge so that the tension applied to the patch 40 may be varied depending upon which projection the elastic member 46 engages.

While the preferred embodiments have been described, variations thereto will occur to those skilled in the art within the scope of the present inventive concepts which are delineated by the following claims.

What is claimed is:

1. A splint for use in carpal tunnel syndrome treatment comprising a support plate adapted to be mounted on the back of the wrist and hand of a patient, securing means for securing said support plate to the wrist and hand, adhesive patch means adapted to be secured to skin on the opposite side of the wrist from the support plate, bridge means mounted on said support plate and extending in a raised manner over the side of the wrist opposite said support plate, and elastic means adjustably connected to said adhesive patch means and said bridge means for applying a negative pressure to the skin of a patient.

2. A splint as set forth in claim 1, wherein said support plate is formed of a semi-rigid material curved to conform to the wrist and hand.

3. A splint as set forth in claim 1, further comprising cushioning means mounted on said support plate between said support plate and the wrist and the hand of the patient to prevent irritation thereof.

4. A splint as set forth in claim 1, further comprising a plurality of perforations in said support plate for purposes of ventilation.

5. A splint as set forth in claim 1, wherein said elastic means is comprised of an elastic loop having a hook thereon for engagement with said patch means and said bridge means is provided with a plurality of fastening means for selective engagement by said elastic loop to control pressure applied to the patch means when secured to the skin.

* * * * *